United States Patent
Müllen et al.

[11] Patent Number: 5,986,099
[45] Date of Patent: Nov. 16, 1999

[54] SUBSTITUTED QUATERRYLENE TETRACARBOXYLIC ACID DIIMIDES

[75] Inventors: Klaus Müllen; Heribert Quante, both of Köln; Arno Böhm, Mannheim, all of Germany

[73] Assignees: BASF Aktiengesellschaft, Ludwigshafen; Max-Planck-Gesellschaft zur Foerderung der Wissenschaften e.V. Berlin, Munich, both of Germany

[21] Appl. No.: 08/860,928

[22] PCT Filed: Jan. 12, 1996

[86] PCT No.: PCT/EP96/00118

§ 371 Date: Jul. 21, 1997

§ 102(e) Date: Jul. 21, 1997

[87] PCT Pub. No.: WO96/22332

PCT Pub. Date: Jul. 25, 1996

[30] Foreign Application Priority Data

Jan. 20, 1995 [DE] Germany .................. 195 01 576

[51] Int. Cl.[6] .................. C09B 5/62; C07D 221/18
[52] U.S. Cl. .................. 546/26; 546/40; 8/636; 8/648
[58] Field of Search .................. 546/26; 8/636, 8/648

[56] References Cited

U.S. PATENT DOCUMENTS

| | | | |
|---|---|---|---|
| 1,715,430 | 6/1929 | Schmidt et al. | 502/407 |
| 4,846,892 | 7/1989 | Henning et al. | 106/478 |
| 5,405,962 | 4/1995 | Muellen et al. | 546/27 |

FOREIGN PATENT DOCUMENTS 4236885  5/1994  Germany .

OTHER PUBLICATIONS

Nagao, Y. et al, Dyes and Pigments, 1991, 16, pp. 19–25.
Quante, H. et al, Angew. Chem. Int. Ed. Engl., 1995, 34(12), 1323–1325.
Seybold, G. et al, Dyes and Pigments, 1989, 11(4), pp. 303–317.

Primary Examiner—Alan L. Rotman
Assistant Examiner—Garth M. Dahlen
Attorney, Agent, or Firm—Oblon, Spivak, McClelland, Maier & Neustadt, P.C.

[57] ABSTRACT

Quaterrylenetetracarboxylic diimides I

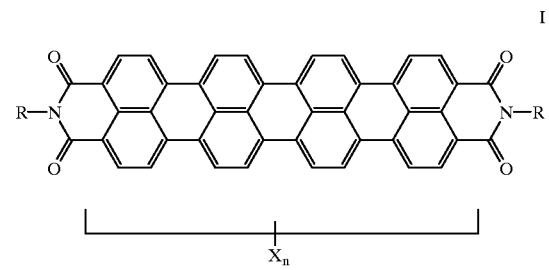

where
R is hydrogen;
  $C_1$–$C_{30}$-alkyl whose carbon chain may be interrupted by one or more of —O—, —S—, —$NR^1$—, —CO— and/or —$SO_2$— and which may be monosubstituted or polysubstituted by cyano, $C_1$–$C_6$-alkoxy or a 5-, 6- or 7-membered heterocyclic radical which is attached via a nitrogen atom and which may contain further heteroatoms and may be aromatic, where
  $R^1$ is hydrogen or $C_1$–$C_6$-alkyl;
  $C_5$–$C_8$-cycloalkyl whose carbon skeleton may be interrupted by one or more of —O—, —S— and/or —$NR^1$—;
  aryl or hetaryl, which may each be monosubstituted or poly-substituted by $C_1$–$C_{18}$-alkyl, $C_1$–$C_6$-alkoxy, cyano, —$CONHR^2$, —$NHCOR^2$ and/or aryl- or hetaryl-azo, which may each be substituted by $C_1$–$C_{10}$-alkyl, $C_1$–$C_6$-alkoxy or cyano, where
  $R^2$ is hydrogen; $C_1$–$C_{18}$-alkyl; aryl or hetaryl, which may each be substituted by $C_1$–$C_6$-alkyl, $C_1$–$C_6$-alkoxy, halogen or cyano;
X is halogen; $C_1$–$C_{18}$-alkyl; aryloxy, arylthio, hetaryloxy or hetarylthio, which may each be substituted by $C_1$–$C_4$-alkyl or $C_1$–$C_4$-alkoxy;
n is from 2 to 12,
their preparation and use as pigments or fluorescent dyes.

9 Claims, No Drawings

SUBSTITUTED QUATERRYLENE TETRACARBOXYLIC ACID DIIMIDES

This application is a 371 of PCT/EP96/00118 filed Jan. 12, 1996.

The present invention relates to novel quaterrylenetetracarboxylic diimides of the general formula I

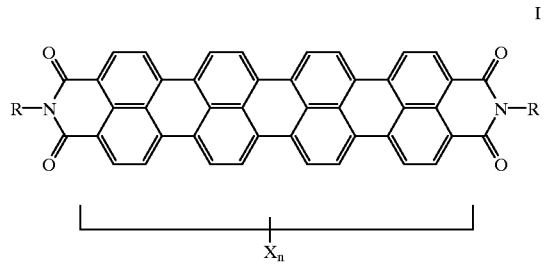

I where
R is hydrogen;
  $C_1$–$C_{30}$-alkyl whose carbon chain may be interrupted by one or more of —O—, —S—, —NR$^1$—, —CO— and/or —SO$_2$— and which may be monosubstituted or polysubstituted by cyano, $C_1$–$C_6$-alkoxy or a 5-, 6- or 7-membered heterocyclic radical which is attached via a nitrogen atom and which may contain further heteroatoms and may be aromatic, where
    R$^1$ is hydrogen or $C_1$–$C_6$-alkyl;
  $C_5$–$C_8$-cycloalkyl whose carbon skeleton may be interrupted by one or more of —O—, —S— and/or —NR$^1$—;
  aryl or hetaryl, which may each be monosubstituted or poly-substituted by $C_1$–$C_{18}$-alkyl, $C_1$–$C_6$-alkoxy, cyano, —CONHR$^2$, —NHCOR$^2$ and/or aryl- or hetaryl-azo, which may each be substituted by $C_1$–$C_{10}$-alkyl, $C_1$–$C_6$-alkoxy or halogen, where
    R$_2$ is hydrogen; $C_1$–$C_{18}$-alkyl; aryloxy, arylthio, hetaryloxy or hetarylthio, which may each be substituted by $C_1$–$C_4$-alkyl or $C_1$–$C_4$-alkoxy;
X is halogen; $C_1$–$C_{18}$-alkyl; aryloxy, arylthio, hetaryloxy or hetarylthio, which may each be substituted by $C_1$–$C_4$-alkyl or $C_1$–$C_4$-alkoxy;
n is from 2 to 12.

The invention also relates to the preparation of these quaterrylenetetracarboxylic diimides and to their use as fluorescent dyes or pigments.

Lastly the invention relates to novel 9-haloperylene-3,4-dicarbimides of the general formula III

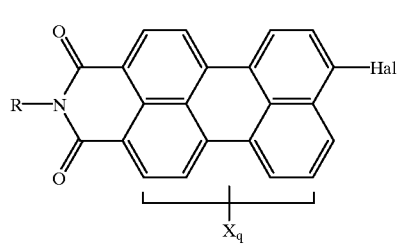

III where R and X are each as defined above, Hal is halogen and q is from 2 to 4, as intermediates for the quaterrylenetetracarboxylic diimides I.

EP-A-596 292 describes with reference to N,N'-didodecylquaterrylene-3,4:13,14-tetracarboxylic diimides the preparation of unsubstituted quaterrylenetetracarboxylic diimides (formula I: n=0; R=n-$C_{12}H_{25}$) and their suitability for use as fluorescent dyes and pigments.

Starting from N-dodecylperylene-3,4,9,10-tetracarboxylic 3,4-imide 9,10-anhydride, decarboxylation in potassium hydroxide solution under superatmospheric pressure and at elevated temperature gives N-dodecylperylene-3,4-dicarbimide, which is brominated to N-dodecyl-9-bromoperylene-3,4-dicarbimide. This is converted by elimination of bromine in the presence of an inert diluent and of an organometallic catalyst to the corresponding biperylene derivative, where it is finally converted by heating in an alkali medium in the presence of an oxidizing agent into the abovementioned quaterrylene derivative.

However, EP-A-596 292 does not disclose any way of preparing substituted quaterrylenetetracarboxylic diimides I (hereinafter shortened to "quaterrylimides") which, however, are of special interest, since specific substitution makes it possible for the application properties (eg. solubility, hydrophilicity, lipophilicity, absorption and emission characteristics) to be predetermined and varied.

It is an object of the present invention to provide novel, substituted quaterrylimides which shall have advantageous application properties (including in the case of fluorescent dyes for example good solubility in the application media) and hence to provide means for optimum adaptation to the particular intended use.

We have found that this object is achieved by the quaterrylimides of the above-defined formula I.

Preferred quaterrylimides I are revealed in the subclaims.

We have also found various processes for preparing the quaterrylimides I, which are likewise revealed in the claims.

Finally, the present invention provides for the use of the quaterrylimides I as pigments or fluorescent dyes.

Last but not least, the 9-haloperylene-3,4-dicarbimides of the above-defined formula III have been found to be useful as intermediates for the preparation of the quaterrylimides I.

Any alkyl appearing in the formulae I and Ia may be straight-chain or branched. Substituted aryl may generally include up to 3, preferably 1 or 2, of the substituents mentioned.

Specific examples of suitable radicals R$^1$ and X (and of their substituents) are:

methyl, ethyl, propyl, isopropyl, butyl, isobutyl, sec-butyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above designations isooctyl, isononyl, isodecyl and isotridecyl are trivial names derived from the oxo process alcohols—cf. Ullmann's Encyklopädie der technischen Chemie, 4th edition, volume 7, pages 215 to 217, and volume 11, pages 435 and 436);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 4,7-dithiaoctyl, 4,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

propan-2-on-1-yl, butan-3-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonylethyl, 2-butylsulfonylethyl, 2- and 3-ethylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2-hydroxypropyl, 1-hydroxyprop-2-yl, 2- and 4-hydroxybutyl, 1-hydroxybut-2-yl and 8-hydroxy-4-oxaoctyl, 2-cyanoethyl, 3-cyanopropyl, 2-methyl-3-ethyl-3-cyanopropyl, 7-cyano-7-ethylheptyl and 4-methyl-7-methyl-7-cyanoheptyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

formylamino, acetylamino, propionylamino and benzoylamino; chlorine, bromine and iodine;

phenylazo, 2-naphthylazo, 2-pyridylazo and 2-pyrimidylazo;

cyclopentyl, cyclohexyl, cycloheptyl, cyclooctyl, 2-dioxanyl, 4-morpholinyl, 2- and 3-tetrahydrofuryl, 1-, 2- and 3-pyrrolidinyl and 1-, 2-, 3- and 4-piperidyl;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5 and 2,6-diisobutylphenyl, 2,4,6-triisobutylphenyl, 2-, 3- and 4-sec-butylphenyl, 2,4-, 3,5- and 2,6-di-sec-butylphenyl and 2,4,6-tri-sec-butylphenyl; 2-, 3- and 4-methoxyphenyl, 2,4-, 3,5- and 2,6-dimethoxyphenyl, 2,4,6-trimethoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxyamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

In the novel processes for preparing the ring-substituted quaterrylimides I, the starting material is in each case a perylene-3,4-dicarbimide II (hereinafter shortened to "perylimide"). Depending on the substitution pattern the quaterrylimides I are to have, the starting material is suitably a perylene-3,4-dicarbimide II which is either unsubstituted or already substituted on the perylene nucleus.

Quaterrylimides of the formula Ia

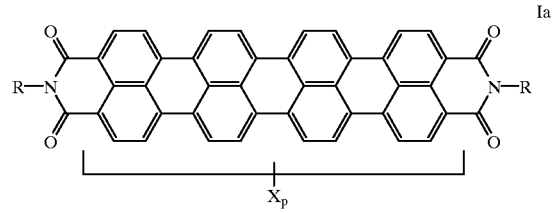

which carry 4 or 8 of the substituents X, in positions 1,7,10,16 and 1,7,11,17 or 1,6,7,10,11,16,17,20, are advantageously obtained starting from a substituted perylimide of the formula IIa IIa

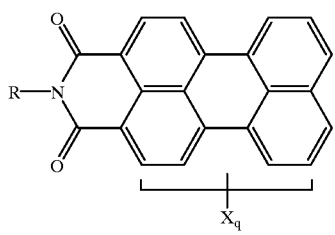

which already carry 2 or 4 of these substituents X, in position 1,7 or 1,6,7,12.

Quaterrylimides of the formula Ib

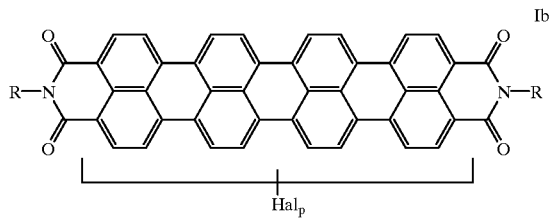

which contain 4 or 8 halogen atoms (preferably chlorine or bromine), in positions 1,6,11,16 or 1,6,7,10,11,16,17,20, are obtained according to the invention by selective halogenation of the unsubstituted perylimides of the formula IIb

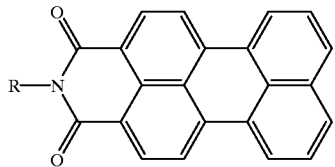

The number of 8 substituents is achieved in particular in the case of chlorinated products, which may of course also contain just 4 chlorine atoms, while bromination generally brings about a substituent number of 4, in each case (especially in the case of the bromination) selectively in the positions mentioned.

Quaterrylimides of the formula Ic

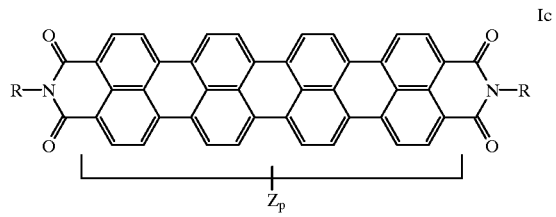

which are substituted by 4 or 8 substituents Z (aryloxy, arylthio, hetaryloxy or hetarylthio, which may each be substituted by $C_1$–$C_4$-alkyl or $C_1$–$C_4$-alkoxy, preferably phenoxy or pyrimidyloxy), in the positions 1,6,11,16 or 1,6,7,10,11,16,17,20 mentioned for the quaterrylimides Ib, are likewise preparable according to the invention from the unsubstituted perylene-3,4-dicarbimides IIb by first halogenating the perylimides IIb and then subjecting them to a nucleophilic substitution (replacement of the halogen atom by the radicals Z).

Quaterrylimides of the formula Id

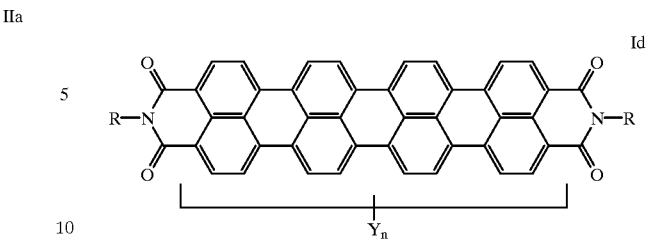

which carry 2, 4, 6, 8 or 12 substituents Y (halogen or radicals Z as mentioned to give the quaterrylimides of the formula Ic), preferably in the positions 1,6; 1,7,8,18; 1,7,9, 11,17,19; 1,6,7,10,11,16,17,20 or 1,6,7,8,9,10,11,16,17,18, 19,20, can be obtained by halogenation (with nucleophilic replacement) of the unsubstituted quaterrylimides Id' (n=0) which like the substituted quaterrylimides Ia–Ic of the invention are likewise obtainable from appropriate perylimides II by conversion thereof into 9-haloperylimides (in particular 9-bromoperylimides) III, coupling of two 9-haloperylimides to corresponding biperylenes IV and oxidation thereof to the quaterrylimides I.

The perylene-3,4-dicarbimides II used as starting materials in the preparation processes of the present invention are described in German Patent Application 195 01 737.4 and can with advantage be prepared, and if desired purified, by the processes likewise presented therein.

According to that reference, the perylimides II are prepared by reacting the appropriately substituted perylene-3, 4,9,10-tetracarboxylic acids or anhydrides, especially the dianhydrides, with the desired primary amines ($RNH_2$).

The perylene-3,4,9,10-tetracarboxylic acids and anhydrides can in turn be obtained by halogenation and if desired subsequent replacement of the halogen atoms by aryloxy, arylthio, hetaryloxy, hetarylthio or alkyl radicals.

The particularly interesting, 1,7-disubstituted perylene-3, 4,9,10-tetracarboxylic acids and anhydrides are, as described in German Patent applications 195 47 209.8 and 195 47 210.1, obtainable by a multistage process starting from 1,7-dibromoperylene-3,4,9,10-tetracarboxylic acid or dianhydride prepared by selective bromination of perylene-3,4,9,10-tetracarboxylic acid or dianhydride in 100% strength by weight sulfuric acid at from 80 to 90° C. These are reacted in the presence of a polar aprotic solvent such as N-methylpyrrolidone and optionally of an imidation catalyst, for example of an organic or inorganic acid or of a transition metal salt, with a primary amine to form the corresponding 1,7-dibromoperylene-3,4,9,10-tetracarboxylic diimide, which is then reacted either in the presence of an inert aprotic solvent such as N-methylpyrrolidone or of a nonnucleophilic or only weakly nucleophilic base, for example sodium carbonate or potassium carbonate, with an aromatic alcohol or thioalcohol or else in the presence of an aprotic solvent such as tetrahydrofuran, of a palladium complex as catalyst and of a copper salt as cocatalyst and of a base, for example piperidine, with a 1-alkyne. In the last case, 1,7-disubstituted perylene-3,4,9,10-tetracarboxylic diimides are obtained which contain unsaturated bonds in the substituent $R^2$ which are reducible by subsequent stirring in a hydrogen atmosphere or by catalytic reduction with hydrogen. In a last reaction step, the either 1,7-diaroxy-, -diarlthio- or -dialkyl-substituted perylene-3,4,9,10-tetracarboxylic diimide is then saponified in the presence of a polar protic solvent such as isopropanol and of a base, for example sodium hydroxide or potassium hydroxide, to the 1,7-disubtituted perylene-3,4,9, 10-tetracarboxylic acid or dianhydride.

The reaction of the perylene-3,4,9,10-tetracarboxylic acids or anhydrides with the primary amines RNH$_2$ is carried out by the process described in German Patent Application 195 01 737.4 in the presence of a tertiary nitrogen-base compound as solvent and of a transition metal or transition metal salt as catalyst.

Examples of suitable nitrogen bases mentioned are cyclic imides such as N-methylpyrrolidone, tertiary aliphatic amines NR$^3$ whose alkyl radicals R have from 4 to 8 carbon atoms, such as trihexylamine, and in particular aromatic heterocycles such as quinaldine, isoquinoline and in particular quinoline.

The amount of solvent will usually range from 2 to 20 kg, preferably from 6 to 12 kg, per kg of perylene-3,4,9,10-tetracarboxylic dianhydride.

The catalysts used are in particular the transition metals iron and especially zinc and copper and also in particular their inorganic and organic salts, preferably copper(I) oxide, copper(II) oxide, copper(I) chloride, copper(II) acetate, zinc acetate and zinc propionate.

Typically from 5 to 80% by weight of catalyst are used, based on the perylene-3,4,9,10-tetracarboxylic dianhydride. Preferred amounts range from 10 to 25% by weight in the case of the copper compounds and from 40 to 60% by weight in the case of the zinc salts, likewise based on the anhydride.

Suitable primary amines for this process include all primary amines which are stable at the reaction temperature, preferably those whose boiling point at the reaction pressure is above the reaction temperature.

The reaction temperature is generally from 120 to 250° C., in particular from 170 to 235 ° C., and it is said to be advisable to work under a protective gas (eg. nitrogen) not only at atmospheric pressure but also at a superatmospheric pressure of customarily up to 10 bar.

The molar ratio used there between the starting compounds amine and anhydride is generally from 0.8:1 to 6:1. For the atmospheric reaction it is preferably from 0.8:1 to 1.2:1, while for the superatmospheric reaction it is in particular from 2:1 to 4:1.

If the (crude) products obtained by this process do not meet the desired purity requirements for the present reaction (the products obtained generally having purities $\geq$80%), they can be additionally subjected to the purification process likewise described.

In the purification process of the reference, the crude perylene-3,4-dicarbimide products are initially heated for about 10–60 minutes in usually from 3 to 10, preferably from 5.5 to 6.5, times the weight of N-methylpyrrolidone (NMP in short) to convert them into NMP adducts.

Suitable temperatures range in general from 140 to 200° C., preferably from 160 to 180° C.

If the imide was already prepared in NMP as solvent, this step can be dispensed with, of course.

The isolated NMP adducts are subsequently subjected to alkaline purification treatment in the presence of an organic diluent at about 50–150° C., preferably 60–120° C. If desired, the alkaline treatment can be followed by an acid aftertreatment.

Suitable diluents include not only inert aromatic solvents such as toluene and xylene but also, with preference, alcohols which can be monohydric or polyhydric, for example aromatic alcohols such as phenol and benzyl alcohol and aliphatic alcohols, not only glycols and glycol ethers, such as ethylene glycol, propylene glycol and butylglycol but also, in particular, $C_2$–$C_6$-alcohols such as ethanol, propanol, butanol, pentanol and hexanol, which may each also be branched, such as, preferably, isopropanol.

In general, the diluent is used in an amount of from 40 to 200 kg, in particular from 80 to 120 kg, per kg of NMP adduct.

Suitable bases include not only sterically hindered nitrogen bases, such as diazabicycloundecene and diazabicyclo [2.2.2]octane, but especially alkali metal hydroxides, such as sodium hydroxide and in particular potassium hydroxide, which are advantageously used mixed with water, and alkali metal salts of secondary and tertiary aliphatic (preferably $C_3$–$C_6$)alcohols, such as sodium tert-butoxide and in particular potassium tert-butoxide.

It is customary to use from 2 to 15 kg of base per kg of NMP adduct, preferably from 5 to 7 kg, in particular about 6 kg, of dry alkali metal hydroxide or from 0.5 to 1.5 kg, in particular from 0.7 to 1 kg, of alkoxide or nitrogen base.

If desired, it is possible to follow this up with an additional acid treatment by suspending the undried filter cake in a dilute inorganic acid, for example 4–6% strength by weight hydrochloric acid (about 4–6 kg of acid per kg of filter cake), and the purified imide II can then be isolated in a conventional manner.

In all versions of the preparation according to the present invention, the first step a) is to halogenate the starting perylimide II. Depending on the quaterrylimides I desired, either only the 9-position of the perylimide is halogenated (preferably brominated) (in cases Ia and Id) or, in addition to the 9-position, 2 or 4 further positions (1- and 6- position or 1-, 6-, 7- and 10-position; syn-halogenation) are halogenated (in cases Ib and Ic), to obtain the halogenated perylimides of the formulae IIIa, IIIb and IIId.

What is particularly important is that the substituents R and X are not attacked by halogen.

The halogenation a) according to the present invention is always carried out in the presence of an inert diluent.

Suitable diluents include not only halogenated aromatics such as chlorobenzene, dichlorobenzene and trichlorobenzene but also, for example, halohydrocarbons, especially methanes and ethanes, such as tribromomethane, tetrachloromethane, tetrabromomethane, 1,2-dichlor-, 1,1-dibromo-, 1,2-dibromo-, 1,1,1-trichloro-, 1,1,2-trichloro-, 1,1,1-tribromo-, 1,1,2-tribromo-, 1,1,1,2-tetrachloro-, 1,1,2,2-tetrachloro-, 1,1,1,2-tetrabromo- and 1,1,2,2-tetrabromo-ethane and especially dichloromethane (methylene chloride) and trichloromethane (chloroform).

The amount of solvent is not critical per se. The amount will generally range from 30 to 200 kg, preferably from 100 to 150 kg, of solvent per kg of perylimide II.

The reaction temperatures generally range from 40 to 140° C. (in particular up to 90° C.). Depending on the desired degree of substitution, it is advantageous to choose lower or higher temperatures from the range mentioned.

If only the 9-position of the perylimide is to be halogenated, temperatures from 40 to 50° C. are preferable, and the use of methylene chloride as solvent is advisable.

If further positions of the perylene structure are to be halogenated, temperatures from 60 to 90° C. are preferred. The trihalogenation is preferably carried out at from 60 to 70° C. and the pentachlorination in general at about 75° C., in which case chloroform and 1,1,2,2-tetrachloromethane (or else chlorobenzene), respectively, make particularly suitable solvents.

The particular advantage here is the selective halogenation, especially bromination, of the abovementioned positions.

The molar ratio of halogen to perylimide II is usually from 10:1 to 100:1, preferably from 40:1 to 60:1 for a bromination and from 10:1 to 40:1 for a chlorination.

The halogenation a) can be carried out not only at atmospheric pressure but also at a superatmospheric pressure up to about 10 bar, and is generally complete after 2–10 h, especially 5–7 h. The reaction times do of course also depend on the desired degree of halogenation, and likewise increase with increasing halogen content.

Step a) is conveniently carried out as follows:

A solution of the perylimide II in the inert solvent is admixed with halogen, if desired under superatmospheric pressure, and heated to the reaction temperature with vigorous stirring. After a reaction time of 2–10 h, cooling and, if applicable, decompression, the reaction mixture is precipitated in water, the excess halogen is removed, for example by admixing with an alkaline sulfite solution, the phase containing the halogenation product is separated off, and the solvent is removed.

The resulting haloperylimides of the formula III

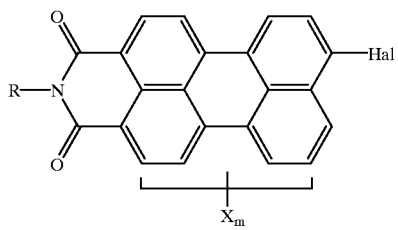

where Hal is chlorine or bromine and m is from 0 to 4 (of the corresponding haloperylimides IIIa–IIId), can be used directly, without further purification, for the next reaction step.

This step (b) comprises in the cases of the quaterrylimides Ia, Ib and Id coupling in each case two of the corresponding haloperylimide molecules III to form a biperylene derivative molecule of the formula IV

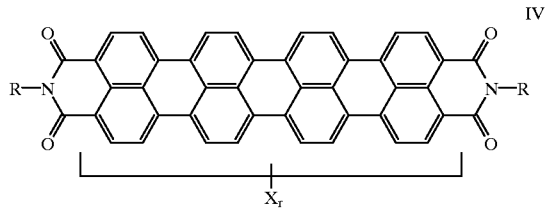

where r is from 0 to 8 (or to the corresponding biperylene derivative molecule IVa, IVb or IVd).

The quaterrylimides Ic first require intermediate step a') which comprises replacing the halogen atoms present in the haloperylimide molecule IIIb, except for the halogen atom in the 9-position, by reaction with a nucleophile of the formula

Z—K where Z is aryloxy, arylthio, hetaryloxy or hetarylthio, which may each be substituted by $C_1$–$C_4$-alkyl or $C_1$–$C_4$-alkoxy, and K is an alkali metal cation or hydrogen, in the presence of a tertiary nitrogen base as solvent and optionally of an inorganic base for radicals Z, to obtain haloperylimides IIIc which are subsequently likewise coupled.

Suitable tertiary nitrogen base solvents include for example aromatic heterocycles, such as quinoline, isoquinoline and quinaldine, and in particular cyclic imides, especially N-methylpyrrolidone.

The amount of solvent is not critical per se, and is generally from 10 to 100 kg, preferably from 20 to 40 kg, per kg of IIIb.

Suitable inorganic bases include for example alkali metal carbonates and hydroxides, in particular potassium carbonate, sodium carbonate, potassium hydroxide and sodium hydroxide, which are preferably used in solid form.

The use of free alcohols or thiols Z—H as nucleophiles generally necessitates from 10 to 100 times, preferably from 15 to 25 times, the molar amount of inorganic base, based on IIIb. If the alkali metal alkoxides or thiolates are used directly, the addition of inorganic base can be dispensed with.

It is advisable to use one mole of nucleophile per mole of halogen atom to be replaced. It is of special importance that the halogen atom in the 9-position of the perylimide is not substituted, which was not to be expected.

The reaction temperature in the substitution step a') is generally from 90 to 160° C., preferably from 100 to 130° C.

A protective gas can be used, for example nitrogen.

Common reaction times are about 2–10 h, in particular 5–7 h.

If desired, the process can be conducted in a cyclic fashion whereby the dehalogenated substitution product formed as a by-product in step a') is rehalogenated (preferably rebrominated) by step a) and then coupled by step b).

Step a') is conveniently carried out as follows:

Haloperylimide IIIb, nucleophile and, if used, solid organic base are initially charged in the solvent and heated, if desired under a protective gas, to the reaction temperature for about 2–10 h. After cooling, the reaction mixture is added with stirring to a dilute inorganic acid, for example dilute hydrochloric acid, and the resulting precipitate is filtered off, subsequently washed with water, dried and, if necessary, chromatographed over silica gel with aromatic solvents such as toluene or halogenated hydrocarbons such as chloroform.

The resulting haloperylimide IIIc can be used in the same way as the other haloperylimides IIIa, IIIb and IIId directly for the coupling step b) to form the biperylene derivatives IV.

The coupling step b) can be carried out analogously to EP-A-596 292 in the presence of an organic metal complex as catalyst, additional free ligand molecules and an inert diluent.

Suitable inert diluents include for example in particular aliphatic carboximides, preferably N,N-dimethylformamide and N,N-dimethylacetamide, aliphatic and cycloaliphatic ethers, such as dimethyl ether, 1,2-dimethoxyethane and tetrahydrofuran, and aromatics, such as benzene, toluene and xylene.

The amount of diluent is not critical per se, and ranges in general from 20 to 100 kg, preferably from 25 to 45 kg, per kg of haloperylimide III.

The organic metal complexes used as catalysts, as well as palladium complexes such as tetrakis(triphenylphosphine) palladium, include in particular nickel complexes, for example bis(triphenylphosphine)nickel(II) chloride, tetrakis (triphenylphosphine)nickel, [1,2-bis(diphenylphosphino) ethane]nickel(II)chloride and preferably bis(1,5-cyclooctadiene)nickel.

The catalysts can also be formed in situ by addition of metal salts or compounds, free ligands, such as cyclooctadiene, bipyridyl, triphenylphosphine, trifluorophosphine, $\eta$-, $\delta$- and $\pi$-bonded olefins, cycloolefins, aromatics and antiaromatics, carbonyls, hydrogen and halogen and also mixtures thereof, and, if necessary, oxidizing or reducing agents.

In general, from 40 to 150 mol %, preferably from 50 to 100 mol %, of organic metal complex are used, based on III.

In general, it is always advisable to ensure the simultaneous presence of free ligand molecules, in particular mixtures of cyclooctadiene and bipyridyl in a molar ratio of from 1:1 to 8:1. Suitable amounts range customarily from 80 to 900 mol %, preferably from 80 to 200 mol %, based on III.

The coupling step b) is advantageously carried out at a temperature of from 40 to 80° C., preferably from 60 to 65° C., and it may also be carried out under protective gas (eg. argon).

The coupling reaction is generally complete after 36–48 h.

Step b) is conveniently carried out as follows:

Haloperylimide III, organometallic catalyst and free ligand molecules are initially charged in the inert diluent and heated, optionally under a protective gas, to the reaction temperature for about 36–48 h. After cooling, the reaction mixture is added to water, which may contain methanol, a dilute inorganic acid, for example dilute hydrochloric acid, is added, and the resulting precipitate is filtered off, subsequently washed with water, dried and, if necessary, chromatographed over silica gel with aromatic solvents such as toluene or xylene.

The resulting biperylene derivatives IV are then converted in step c), analogously to EP-A-596 292, into the quaterrylimides I by heating in the presence of an oxidizing agent and of an alkaline reaction medium.

Suitable oxidizing agents include for example aluminum chloride, iron(III) chloride, manganese dioxide, palladium (II) acetate, vanadium oxytrichloride, copper(II) chloride, sodium formaldehydesulfoxylate and in particular glucose.

In general, from 10 to 50 times, preferably 20 to 35 times, the molar amount of the preferred oxidizing agent glucose is used, based on IV.

The alkaline reaction medium used is conveniently a mixture of an alkali metal hydroxide, especially sodium hydroxide or potassium hydroxide, a $C_1$–$C_4$-alkanol, such as methanol, ethanol, propanol, isopropanol, butanol, isobutanol or sec-butanol.

The amount used per kg of IV is customarily from 60 to 250 kg, preferably from 100 to 160 kg, of alkali metal hydroxide and from 40 to 200 kg, preferably from 70 to 140 kg, of alkanol.

The oxidation c) is advantageously carried out at a temperature of from 60 to 180° C., in particular at from 100 to 130° C., and it is also possible to use a protective gas, for example argon.

The oxidation is generally complete after 1–4 h, especially 1–2.5 h.

Step c) is conveniently carried out as follows:

Biperylene derivative IV, alkali metal hydroxide, alkanol and oxidizing agent are initially charged and heated, optionally under a protective gas, to the reaction temperature for 1–2.5 h. After cooling, the reaction mixture is acidified with aqueous mineral acid, for example hydrochloric acid, and the resulting precipitate is filtered, subsequently washed with water, dried and extracted with inert solvents, such as chloroform, diethyl ether, methyl tert-butyl ether or toluene, to remove any by-products present.

The process leading to the quaterrylimides Id produces in step c) the unsubstituted quaterrylimides Id', which are halogenated subsequently (step d)) and, if desired, can be subjected to a replacement of the halogen atoms by nucleophilic radicals Z (step e)).

The halogenation step d) can be carried out analogously to the halogenation step a), but in 1.5–2 times the amount of solvent and in each case with twice the reaction time.

The decisive requirement is that the halogenation of the quaterrylene molecule Id' produces the anti-halogenation product (eg. 1,7,9,11,17,19-hexabromoquaterrylimide), in contradistinction to step a).

As in step a), the degree of halogenation here too increases with increasing temperature and increasing reaction time.

Replacement step e) can likewise be carried out analogously to the corresponding step a'), but here too from 1.5 to 2 times the amount of solvent should be used and the reaction time should be doubled.

The quaterrylimides I of the present invention are advantageously useful as pigments or fluorescent dyes. They can be used in particular for coloring macromolecular organic materials or else organic/inorganic composites.

Suitable pigments are in particular quaterrylimides of the formula I where R is $C_8$–$C_{20}$-alkyl, phenyl, pyridyl or pyrimidyl, which may each be monosubstituted or polysubstituted by $C_1$–$C_4$-alkyl or monosubstituted by phenylazo or naphthylazo, X is halogen and n from 2 to 8.

Suitable fluorescent dyes in particular are quaterrylimides of the formula I where R is $C_5$–$C_8$-cycloalkyl or phenyl, pyridyl or pyrimidyl, which each are monosubstituted or polysubstituted by $C_1$–$C_4$-alkoxy, —CONHR$^2$ or —NHCOR$^2$ (R$^2$: $C_1$–$C_4$-alkyl or phenyl which may be substituted by $C_1$–$C_4$-alkyl or $C_1$–$C_4$-alkoxy), X is phenoxy, phenylthio, pyrimidyloxy or pyrimidylthio which may be substituted by $C_1$–$C_4$-alkyl, and n is from 2 to 8.

EXAMPLES

A1) Preparation of novel 1,6,9-tribromoperylene-3,4-dicarbimides of the formula IIIa'

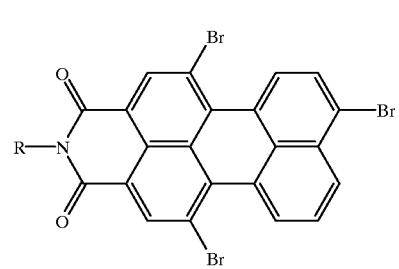

Example 1a

A solution of 12 g (25 mmol) of N-(2,6-diisopropylphenyl)perylene-3,4-dicarbimide in 1.5 l of chloroform was admixed with 75 ml (1.46 mol) of bromine, heated with vigorous stirring to the refluxing temperature (about 61° C.) and held at that temperature for 6 h.

After cooling down to room temperature, the reaction mixture was added with stirring to a solution of 15 g of potassium hydroxide and 10 g of sodium sulfite in 2 l of water and admixed a little at a time with 6 g of potassium hydroxide and 4 g of sodium sulfite until the excess bromine had all been removed (evident from the change of color from dark reddish brown to bright orange). The organic phase was separated off and the brominated perylimide IIIa' was isolated by removing all the solvent by stripping.

This gave 19.5 g of N-(2,6-diisopropylphenyl)-1,6,9-tribromoperylene-3,4-dicarbimide in the form of an orange solid having a purity of 84% and a melting point >300° C., which corresponds to a yield of 91%.

Examples 2a to 5a

The method of Example 1a was also employed to prepare the bromoperylimides IIIa' mentioned in Table A by reaction of the corresponding unhalogenated perylimides with bromine. Example 1a is also listed for clarity.

TABLE A

| Ex. | R | Yield in % | Color | mp. [° C.] |
|---|---|---|---|---|
| 1a | 2,6-Diisopropylphenyl | 91 | orange | >300 |
| 2a | Dodecyl | 92 | red | >300 |
| 3a | 4-tert-Butylphenyl | 100 | bright red | >300 |
| 4a | 4-Phenylazophenyl | 95 | dark red | >350 |
| 5a | 2-Methylphenyl | 98 | bright red | >300 |

A2) Preparation of novel 1,7,9-tribromoperylene-3,4-dicarbimides of the formula IIIa"

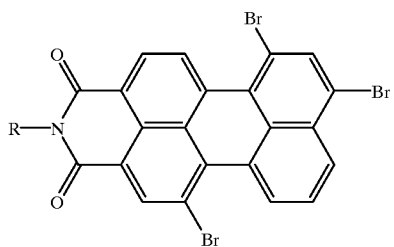

Example 6a

R=2,6-diisopropylphenyl 15.9 g (25 mmol) of N-(2,6-diisopropylphenyl)-1,7-dibromoperylene-3,4-dicarbimide were reacted with 75 ml (1.46 mol) of bromine as described in Example 1a, but at 40° C. in 1.2 l of methylene chloride as solvent.

The 1,7-dibromoperylene-3,4,9,10-tetracarboxylic dianhydride used as precursor for the preparation of the 1,7-dibrominated perylimide was obtained by selective bromination of perylene-3,4,9,10-tetracarboxylic dianhydride.

A mixture of 292.5 g (0.75 mol) of perylene-3,4,9,10-tetracarboxylic dianhydride (purity>98%) and 4420 g of 100% strength by weight sulfuric acid was heated to 85° C. after stirring for 12 hours and the subsequent addition of 7 g of iodine. 262.5 g (1.64 mol) of bromine were then added dropwise over 8 h. After cooling down to room temperature and displacing the excess bromine by means of nitrogen, the sulfuric acid concentration of the reaction mixture was reduced to 86% by weight by adding a total of 670 g of water a little at a time over 1 h. After cooling the reaction mixture, which had heated up to 85° C., to room temperature, the precipitated product was filtered off on a G4 glass frit, washed with 3 kg of 86% by weight sulfuric acid, then resuspended in 5 l of water, filtered again, washed neutral and dried under reduced pressure at 120° C.

The reaction of Example 6a gave 18.5 g of N-(2,6-diisopropylphenyl)-1,7,9-tribromoperylene-3,4-dicarbimide as a reddish orange solid having a purity of 95% and a melting point >300° C., which corresponds to a yield of 98%.

B1) Preparation of novel 1,6-diaryloxy-9-bromoperylene-3,4-dicarbimides of the formula IIIb'

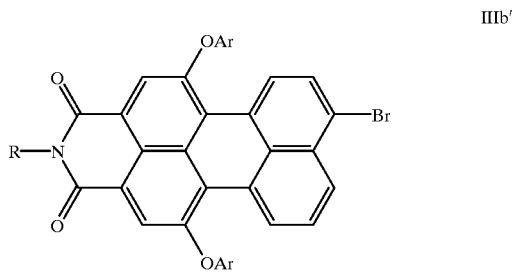

Example 1b

A mixture of 16 g (22 mmol) of the tribromoperylimide of Example 1a, 6.6 g (44 mmol) of 4-tert-butylphenol and 6.9 g (50 mmol) of potassium carbonate in 500 ml of N-methylpyrrolidone was heated at 120° C. for 6 h.

After cooling down to room temperature, the reaction mixture was added with stirring into 2 l of 5:1 w/w water/37% strength by weight hydrochloric acid. The resulting precipitate was filtered off, washed with water, dried and subsequently chromatographed over silica gel (column 12×120 cm) with toluene, the product being eluted as the first, orange-colored fraction.

Recrystallization from methylene chloride/methanol gave 6.3 g of N-(2,6-diisopropylphenyl)-1,6-di(4-tert-butylphenoxy)-9-bromoperylene-3,4-dicarbimide as a red solid of melting point 297° C., which corresponds to a yield of 33%.

Examples Ib' to 4b'

The method of Example 1b was also employed to prepare the perylimides IIb' mentioned in Table B by reacting the corresponding tribromoperylimides IIIa' with phenols

TABLE B

| Ex. | R | Ar | Yield in % | Color | mp. [° C.] |
|---|---|---|---|---|---|
| 1b | 2,6-Diisopropylphenyl | 4-tert-Butylphenyl | 33 | red | 297 |
| 1b' | 2,6-Diisopropylphenyl | Phenyl | 42 | red | >300 |
| 2b | Dodecyl | 4-tert-Butylphenyl | 33 | reddish orange | >300 |
| 3b | 4-tert-Butylphenyl | 4-tert-Butylphenyl | 16 | red | >300 |
| 3b' | 4-tert-Butylphenyl | Phenyl | 26 | red | >300 |

B2) Preparation of novel 1,7-diaryloxy-9-bromoperylene-3,4-dicarbimides of the formula IIIb'

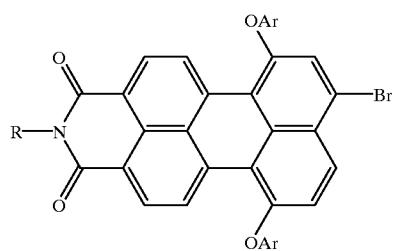

IIIb″

Example 6b

R=2,6-diisopropylphenyl; Ar=4-tert-butylphenyl

The method of Example 1b was employed to react the tribromoperylimide of Example 6a with 4-tert-butylphenol.

This gave 7.4 g of N-(2,6-diisopropylphenyl)-1,7-di(4-tert-butylphenoxy)-9-bromoperylene-3,4-dicarbimide as a red solid of melting point 289° C., which corresponds to a yield of 39%.

C1) Preparation of 1,1',6,6'-tetraaryloxy-3,3',4,4'-biperylenetetracarboxylic diimides IV'

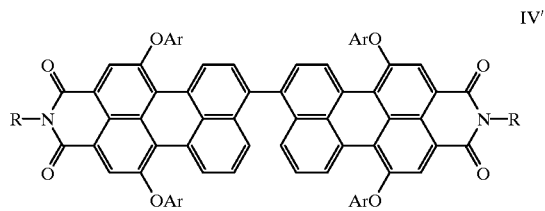

IV'

Example 1c mixture of 385 mg (1.4 mmol) of bis(1,5-cyclooctadiene) nickel, 126 mg (1.17 mmol) of 1,5-cyclooctadiene and 185 mg (1.17 mmol) of 2,2'-bipyridyl in 60 ml of N,N-dimethylformamide was stirred in a 100 ml Schlenk flask at room temperature under argon for 1 h, admixed with 2 g (2.33 mmol) of the bromoperylimide of Example 1b and then stirred at 70° C. for 2 d.

The workup was carried out similarly to Example 1b, except that only 1 l of the water-hydrochloric acid mixture was used and the recrystallization was carried out from methylene chloride.

This gave 1.55 g of N,N'-bis(2,6-diisopropylphenyl)-1,1',6,6'-tetra(4-tert-butylphenoxy)-3,3',4,4'-biperylenetetracarboxylic diimide as a red powder of melting point 259° C., which corresponds to a yield of 86%.

Examples 1c' to 3c'

The method of Example 1c was also employed to prepare the piperylenes IV' mentioned in Table C by coupling the bromoperylimides IIIb'.

TABLE C

| Ex. | R | Ar | Yield in % | Color | mp. [° C.] |
|---|---|---|---|---|---|
| 1c | 2,6-Diiso-propylphenyl | 4-tert-Butyl-phenyl | 86 | red | 259 |

TABLE C-continued

| Ex. | R | Ar | Yield in % | Color | mp. [° C.] |
|---|---|---|---|---|---|
| 1c' | 2,6-Diiso-propylphenyl | Phenyl | 88 | red | >300 |
| 2c | Dodecyl | 4-tert-Butyl-phenyl | 79 | reddish brown | >300 |
| 3c | 4-tert-Butyl-phenyl | 4-tert-Butyl-phenyl | 64 | reddish brown | >300 |
| 3c' | 4-tert-Butyl-phenyl | Phenyl | 65 | reddish brown | >300 |

C2) Preparation of 1,1',7,7'-tetraaroxy-3,3',4,4'-biperylenetetracarbimides IV″

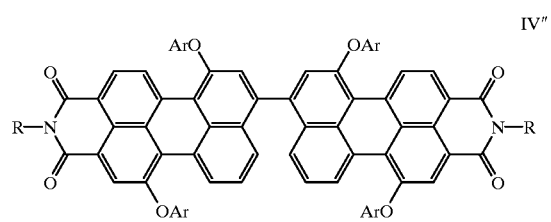

IV″

Example 6c

R=2,6-diisopropylphenyl; Ar=4-tert-butylphenyl

The method of Example 1c was followed to couple the bromoperylimide of Example 6b.

This gave 1.37 g of N,N'-bis(2,6-diisopropylphenyl)-1,1',7,7'-tetra(4-tert-butylphenoxy)-3,3'-4,4'-biperylenetetracarboxylic diimide as a red powder of melting point 273° C., which corresponds to a yield of 76%.

D1) Preparation of novel 1,6,11,16-tetraaryloxyquaterrylene-3,4:13,14-tetracarboxylic diimides I'

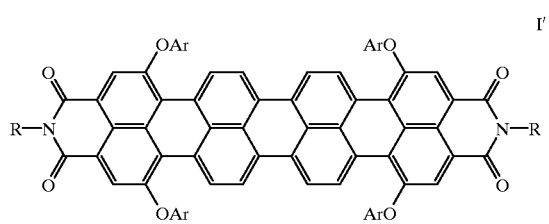

I'

Example 1d

A mixture of 80 g of pulverized potassium hydroxide, 80 ml of ethanol, 6 g of glucose and 500 mg (0.32 mmol) of the biperylene derivative of Example 1c was heated at 120° C. under argon for 2.5 h.

After cooling down to room temperature, the reaction mixture was added to 420 ml of water and admixed with 80 ml of concentrated hydrochloric acid. The resulting precipitate was filtered off and washed successively with saturated aqueous potassium carbonate solution, water, methanol and diethyl ether. The soluble by-products were removed by additional extraction with chloroform.

This gave 421 mg of N,N'-bis(2,6-diisopropylphenyl)-1,6,11,16-tetra(4-tert-butylphenoxy)quaterrylene-3,4:13,14-tetracarboxylic diimide as a green powder of melting point >300° C., which corresponds to a yield of 85%.

These are some analytical data for this quaterrylimide:

$^1$H-NMR (500 MHz, CDCl$_3$): δ=9.09 (d,4H), 8.32 (s,4H), 7.76 (d,4H), 7.41 (t,2H), 7.34 (d,8H), 7.28 (d,4H), 7.00 (d,8H), 2.76 (m,4H), 1.26 (s,36H), 1.13 (d,24H) ppm;

$^{13}$C-NMR (125,5 MHz, CDCl$_3$): δ=163.0, 153.6, 152.9, 147.0, 145.8, 131.2, 130.9, 130.8, 129.4, 129.2, 128.9, 127.7, 127.5, 127.2, 126.4, 125.2, 124.3, 123.9, 122.5, 121.6, 117.4, 34.4, 31.4, 29.2, 24.1 ppm;

IR (KBr): ν=1707 (s,C=O), 1669 (s,C=O) cm$^{-1}$;

UV/VIS (CH$_2$Cl$_2$): λ$_{max}$ (ε)=262 (95819), 271 (97645), 382 (12895), 709 (71931), 781 (166571) nm;

Fluorescence (CH$_2$Cl$_2$): λ$_{max}$=806 nm.

Of particular importance for the use as fluorescent dye is the solubility of the quaterrylimide in organic solvents: 25–30 mg/ml of chloroform at room temperature, 80 mg/ml of tetrachloroethane at 135° C.

By comparison, the unsubstituted N,N'-dodecylquaterrylimide known from EP-A-596 292 is insoluble in both solvents and the analogous, unsubstituted N,N'-bis(2,6-diisopropylphenyl)quaterrylimide almost insoluble (solubility <0.2 mg/ml of chloroform, 1–2 mg/ml of tetrachloroethane).

Also of interest is the bathochromic shift of the longest-wavelength absorption band by 20 nm in the UV/VIS spectrum, compared with the corresponding unsubstituted quaterrylimide.

D2) Preparation of novel 1,7,10,16-tetraaryloxyquaterrylene-3,4:13,14-tetracarboxylic diimides I"

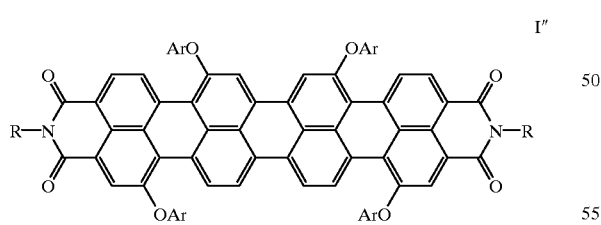

Example 6d

R=2,6-diisopropylphenyl; Ar=4-tert-butylphenyl

The method of Example 1d was followed to oxidize the biperylene if Example 6c.

This gave 318 mg N,N'-bis(2,6-diisopropylphenyl)-1,7,10,16-tetra(4-tert-butylphenoxy)quaterrylene-3,4:13,14-tetracarboxylic diimide as a bluish green powder of melting point >300° C., which corresponds to a yield of 64%.

D3) Preparation of N,N-bis(2,6-diisopropylphenyl)-1,7,9,11,17,19-hexabromoquaterrylene-3,4:13,14-tetracarboxylic diimide I'''

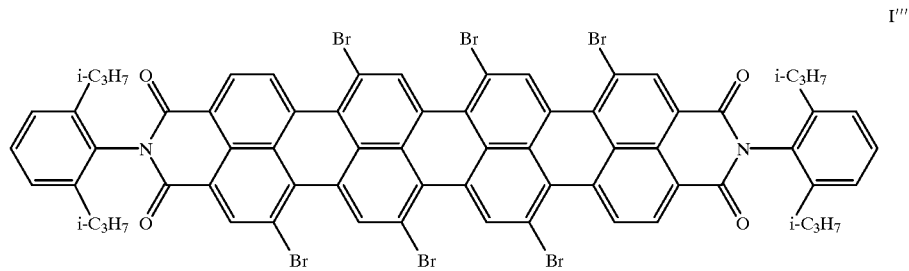

Example 7

1.0 g of unsubstituted N,N'-bis(2,6-diisopropylphenyl) quaterrylimide, obtained by bromination of unsubstituted N-2,6-diisopropylperylene-3,4-dicarbimide to the 9-bromoperylimide similarly to Example 6a, subsequently coupling similarly to Example 1c and oxidation similarly to Example 1d, was brominated similarly to Example 1a except for the doubling of the reaction time to 12 h.

This gave 1.3 g of I''' as a dark red solid having a purity of 85% (15% of tetrabromo product) and a melting point >300° C., which corresponds to a yield of 91%.

We claim:

1. Quaterrylenetetracarboxylic diimides of formula I:

wherein
R is hydrogen;
C$_1$–C$_{30}$-alkyl whose carbon chain optionally is interrupted by one or more of —O—, —S—, —NR$^1$—, —CO— and/or —SO$_2$— and which optionally is monosubstituted or polysubstituted by cyano, C$_1$–C$_6$-alkoxy or a 5-, 6- or 7-membered heterocyclic radical which is attached via a nitrogen atom and which optionally contains additional heteroatoms and optionally is aromatic, where
R$^1$ is hydrogen or C$_1$–C$_6$-alkyl;
C$_5$–C$_8$-cycloalkyl whose carbon skeleton optionally is interrupted by one or more of —O—, —S— and/or —NR$^1$—;
aryl or hetaryl, each of which optionally is monosubstituted or polysubstituted by C$_1$–C$_{18}$-alkyl, C$_1$–C$_6$-alkoxy, cyano, —CONHR$^2$, —NHCOR$^2$ and/or aryl- or hetaryl-azo, each of which optionally is substituted by C$_1$–C$_{10}$-alkyl, C$_1$–C$_6$-alkoxy or halogen, where
R$^2$ is hydrogen; C$_1$–C$_{18}$-alkyl; aryl or hetaryl, each of which optionally is substituted by C$_1$–C$_6$-alkyl, C$_1$–C$_6$-alkoxy, halogen or cyano;

X is halogen; $C_1$–$C_{18}$-alkyl; aryloxy, arylthio, hetaryloxy or hetarylthio, each of which optionally is substituted by $C_1$–$C_4$-alkyl or $C_1$–$C_4$-alkoxy;

n is from 2 to 12.

2. Quaterrylenetetracarboxylic diimides as claimed in claim 1, wherein:

R is $C_8$–$C_{20}$-alkyl whose carbon chain optionally is interrupted by one or more of —O— or —S— and which optionally is monosubstituted or polysubstituted by $C_1$–$C_4$-alkoxy or a 5-, 6- or 7-membered heterocyclic radical which is attached via a nitrogen atom and which optionally contains additional heteroatoms and optionally is aromatic;

$C_5$–$C_8$-cycloalkyl;

phenyl or hetaryl, each of which optionally is monosubstituted or polysubstituted by $C_1$–$C_{12}$-alkyl, $C_1$–$C_4$-alkoxy, —CONHR$^2$ and/or —NHCOR$^2$ and/or monosubstituted by aryl- or hetaryl-azo, each of which optionally is substituted by $C_1$–$C_{10}$-alkyl, $C_1$–$C_6$-alkoxy, halogen or cyano;

X is halogen; phenoxy, phenylthio, pyridyloxy, pyridylthio, pyrimidyloxy or pyrimidylthio, each of which optionally is subtituted by $C_1$–$C_4$-alkyl or $C_1$–$C_4$-alkoxy;

n is from 2 to 8.

3. Quaterrylenetetracarboxylic diimides as claimed in claim 1, wherein:

R is $C_8$–$C_{20}$-alkyl whose carbon chain optionally is interrupted by one or more of —O— and optionally is substituted by $C_1$–$C_4$-alkoxy;

$C_5$–$C_8$-cycloalkyl;

phenyl, pyridyl or pyrimidyl, each of which optionally is monosubstituted or polysubstituted by $C_1$–$C_4$-alkyl, $C_1$–$C_4$-alkoxy, —CONHR$^2$ or —NHCOR$^2$ and/or monosubstituted by phenylazo or naphthylazo, each of which optionally is substituted by $C_1$–$C_4$-alkyl, $C_1$–$C_4$-alkoxy or cyano, where R$^2$ is $C_1$–$C_4$-alkyl or phenyl each of which optionally is substituted by $C_1$–$C_4$-alkyl or $C_1$–$C_4$-alkoxy;

X is halogen; phenoxy, phenylthio, pyrimidyloxy or pyrimidylthio, each of which optionally is substituted by $C_1$–$C_4$-alkyl;

n is from 2 to 8.

4. A process for preparing quaterrylenetetracarboxylic diimides of formula Ia:

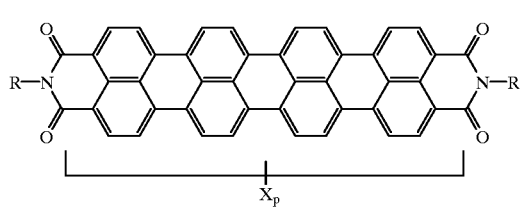

wherein:

R is hydrogen;

$C_1$–$C_{30}$-alkyl whose carbon chain optionally is interrupted by one or more of —O—, —S—, —NR$^1$—, —CO— and/or —SO$_2$— and which optionally is monosubstituted or polysubstituted by cyano, $C_1$–$C_6$-alkoxy or a 5-, 6- or 7-membered heterocyclic radical which is attached via a nitrogen atom and which optionally contains additional heteroatoms and optionally is aromatic, where R$^1$ is hydrogen or $C_1$–$C_6$-alkyl;

$C_5$–$C_8$-cycloalkyl whose carbon skeleton optionally is interrupted by one or more of —O—, —S— and/or —NR$^1$—;

aryl or hetaryl, each of which optionally is monosubstituted or polysubstituted by $C_1$–$C_{18}$-alkyl, $C_1$–$C_6$-alkoxy, cyano, —CONHR$^2$, —NHCOR$^2$ and/or aryl- or hetaryl-azo, each of which optionally is substituted by $C_1$–$C_{10}$-alkyl, $C_1$–$C_6$-alkoxy or halogen, where R$^2$ is hydrogen; $C_1$–$C_{18}$-alkyl; aryl or hetaryl, each of which optionally is substituted by $C_1$–$C_6$-alkyl, $C_1$–$C_6$-alkoxy, halogen or cyano;

X is halogen; $C_1$–$C_{18}$-alkyl; aryloxy, arylthio, hetaryloxy or hetarylthio, each of which optionally is substituted by $C_1$–$C_4$-alkyl or $C_1$–$C_4$-alkoxy;

p is from 4 to 8, which comprises a) reacting perylene-3,4-dicarbimides of formula Ia

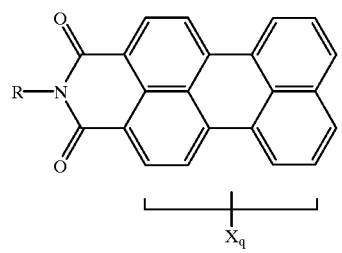

where q is from 2 to 4, with elemental bromine in the presence of an inert diluent at from 40 to 50° C. to form brominated perylimides of formula IIIa:

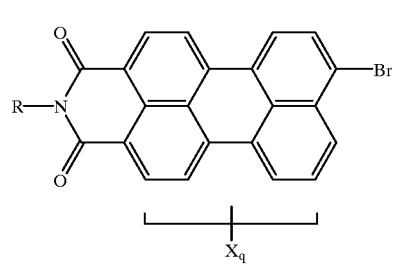

b) coupling the brominated perylimides IIIa in the presence of an organic metal complex as catalyst, free ligand molecules and an inert diluent to form biperylene derivatives of formula IVa:

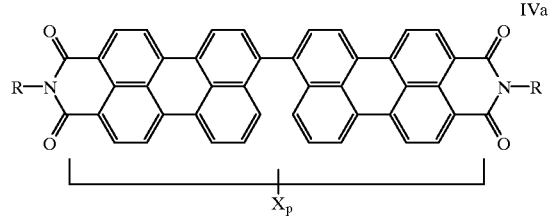

and c) converting the biperylene derivatives IVa by heating in the presence of an oxidizing agent and of an alkaline reaction medium into the quaterrylenetetracarboxylic diimides Ia.

5. A process for preparing quaterrylenetetracarboxylic diimides of formula Ib:

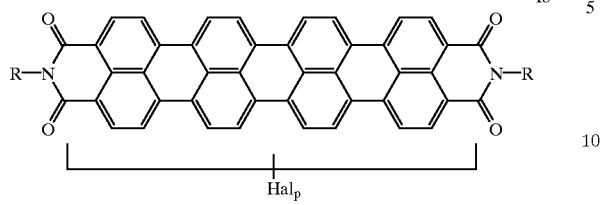

wherein:

R is hydrogen;

C$_1$–C$_{30}$-alkyl whose carbon chain optionally is interrupted by one or more of —O—, —S—, —NR$^1$—, —CO— and/or —SO$_2$— and which optionally is monosubstituted or polysubstituted by cyano, C$_1$–C$_6$-alkoxy or a 5-, 6- or 7-membered heterocyclic radical which is attached via a nitrogen atom and which optionally contains additional heteroatoms and optionally is aromatic, where R$^1$ is hydrogen or C$_1$–C$_6$-alkyl;

C$_5$–C$_8$-cycloalkyl whose carbon skeleton optionally is interrupted by one or more of —O—, —S— and/or —NR$^1$—;

aryl or hetaryl, each of which optionally is monosubstituted or polysubstituted by C$_1$–C$_{18}$-alkyl, C$_1$–C$_6$-alkoxy, cyano, —CONHR$^2$, —NHCOR$^2$ and/or aryl- or hetaryl-azo, each of which optionally is substituted by C$_1$–C$_{10}$-alkyl, C$_1$–C$_6$-alkoxy or halogen, where R$^2$ is hydrogen; C$_1$–C$_{18}$-alkyl; aryl or hetaryl, each of which optionally is substituted by C$_1$–C$_6$-alkyl, C$_1$–C$_6$-alkoxy, halogen or cyano;

Hal is chlorine or bromine;

p is from 4 to 8, which comprises a) reacting perylene-3,4-dicarbimides of formula IIb:

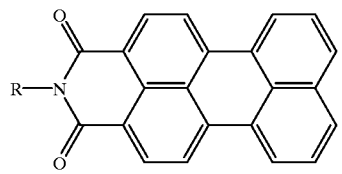

with elemental halogen in the presence of an inert diluent at from 60 to 140° C. to form halogenated perylimides of formula IIIb:

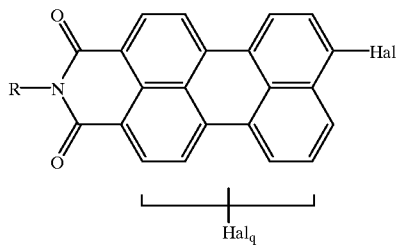

where Hal is bromine or chlorine and q is from 2 to 4, b) coupling the halogenated perylimides IIIb in the presence of an organic metal complex as catalyst, free ligand molecules and an inert diluent to form biperylene derivatives of formula IVb:

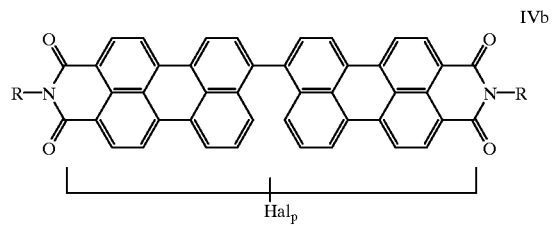

and c) converting the biperylene derivatives IVb by heating in the presence of an oxidizing agent and of an alkaline reaction medium into quaterrylenetetracarboxylic diimides Ib.

6. A process for preparing quaterrylenetetracarboxylic diimides of the formula Ic

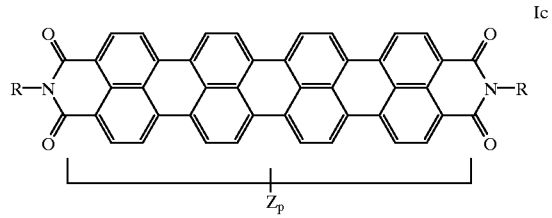

where:

R is hydrogen;

C$_1$–C$_{30}$-alkyl whose carbon chain optionally is interrupted by one or more of —O—, —S—, —NR$^1$—, —CO— and/or —SO$_2$— and which optionally is monosubstituted or polysubstituted by cyano, C$_1$–C$_6$-alkoxy or a 5-, 6- or 7-membered heterocyclic radical which is attached via a nitrogen atom and which optionally contains additional heteroatoms and optionally is aromatic, where R is hydrogen or C$_1$–C$_6$-alkyl;

C$_5$–C$_8$-cycloalkyl whose carbon skeleton optionally is interrupted by one or more of —O—, —S— and/or —NR$^1$;

aryl or hetaryl, each of which optionally is monosubstituted or polysubstituted by C$_1$–C$_{18}$-alkyl, C$_1$–C$_6$-alkoxy, cyano, —CONHR$^2$, —NHCOR$^2$ and/or aryl- or hetaryl-azo, each of which optionally is substituted by C$_1$–C$_{10}$-alkyl, C$_1$–C$_6$-alkoxy or halogen, wherein R² is hydrogen; C₁–C₁₈-alkyl; aryl or hetaryl, each of which optionally is substituted by C₁–C₆-alkyl, C₁–C₆-alkoxy, halogen or cyano;

Z is aryloxy, arylthio, hetaryloxy or hetarylthio, each of which optionally is substituted by C₁–C₄-alkyl or C₁–C₄-alkoxy;

p is from 4 to 8, which comprises a) reacting perylene-3,4-dicarbimides of formula IIb

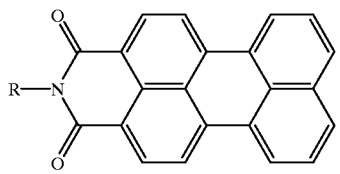
IIb with elemental halogen in the presence of an inert diluent at from 60 to 140° C. to form halogenated perylimides of formula IIIb;

where Hal is bromine or chlorine and q is from 2 to 4,

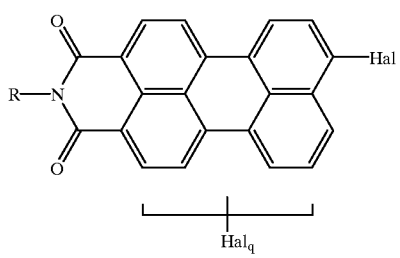
IIIb a') converting the halogenated perylimides IIIb in the presence of a tertiary nitrogen base as solvent and optionally of an inorganic base with nucleophiles of the formula:

Z—K where K is an alkali metal cation or hydrogen, into substituted perylimides of formula IIIc:

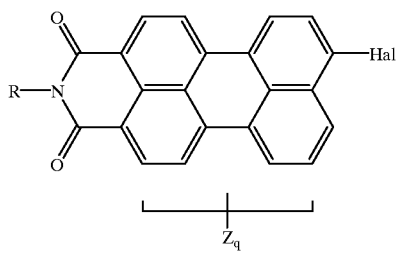
IIIc b) coupling the substituted perylimides IIIc in the presence of an organic metal complex as catalyst, free ligand molecules and an inert diluent to form biperylene derivatives of formula IVc:

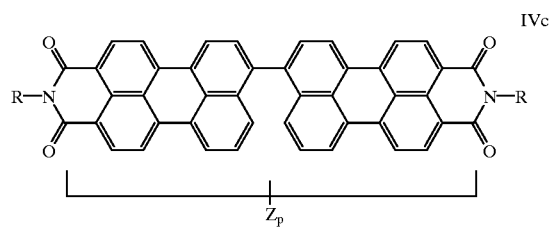
IVc and c) converting the biperylene derivatives IVc by heating in the presence of an oxidizing agent and of an alkaline reaction medium into the quaterrylenetetracarboxylic diimides Ic.

7. A process for preparing quaterrylenetetracarboxylic diimides of formula Id:

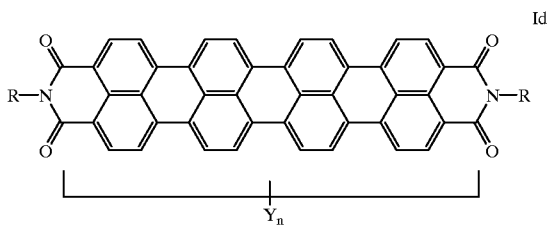
Id where:

R is hydrogen;

C₁–C₃₀-alkyl whose carbon chain optionally is interrupted by one or more of —O—, —S—, —NR¹—, —CO— and/or —SO₂— and which optionally is monosubstituted or polysubstituted by cyano, C₁–C₆-alkoxy or a 5-, 6- or 7-membered heterocyclic radical which is attached via a nitrogen atom and which optionally contains additional heteroatoms and optionally is aromatic, where R¹ is hydrogen or C₁–C₆-alkyl;

C₅–C₈-cycloalkyl whose carbon skeleton optionally is interrupted by one or more of —O—, —S— and/or —NR¹—;

aryl or hetaryl, each of which optionally is monosubstituted or polysubstituted by C₁–C₁₈-alkyl, C₁–C₆-alkoxy, cyano, —CONHR², —NHCOR² and/or aryl- or hetaryl-azo, each of which optionally is substituted by C₁–C₁₀-alkyl, C₁–C₆-alkoxy or halogen, wherein R² is hydrogen; C₁–C₁₈-alkyl; aryl or hetaryl, each of which optionally is substituted by C₁–C₆-alkyl, C₁–C₆-alkoxy, halogen or cyano;

Y is halogen; aryloxy, arylthio, hetaryloxy or hetarylthio, each of which optionally is substituted by C₁–C₄-alkyl or C₁–C₄-alkoxy;

n is from 2 to 12, which comprises a) reacting perylene-3,4-dicarbimides of formula IIb:

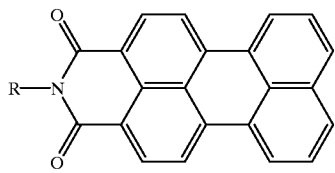

IIb with elemental bromine in the presence of an inert diluent at from 40 to 50° C. to form brominated perylimides of formula IIId:

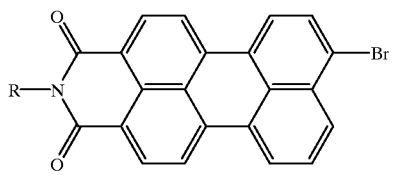

IIId b) coupling the brominated perylimides IIId in the presence of an organic metal complex as catalyst, free ligand molecules and an inert diluent to form biperylene derivatives of formula IVd;

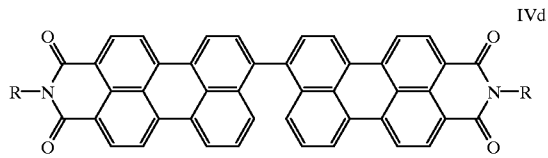

IVd c) converting the biperylene derivatives IVd by heating in the presence of an oxidizing agent and of an alkaline reaction medium into unsubstituted quaterrylenetetracarboxylic diimides Id'

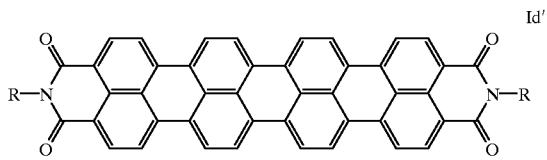

Id' d) reacting the unsubstituted quaterrylenetetracarboxylic diimides Id' with elemental halogen in the presence of an inert diluent at from 60 to 140° C. to form the halogenated quaterrylenetetracarboxylic diimides Id (Y:Hal), and optionally e) converting the halogenated quaterrylenetetracarboxylic diimides by reaction with nucleophiles of the formula:

Z—K where Z is aryloxy, arylthio, hetaryloxy or hetarylthio, each of which optionally is substituted by $C_1$–$C_4$-alkyl or $C_1$–$C_4$-alkoxy, and K is an alkali metal cation or hydrogen, in the presence of an inorganic base and of a tertiary nitrogen base into the quaterrylenetetracarboxylic diimide of formula Id where Y is Z.

8. A fluorescent dye or pigment comprising quaterrylenetetracarboxylic diimides of formula I as claimed in claim 1.

9. Quaterrylenetetracarboxylic diimides of formula I:

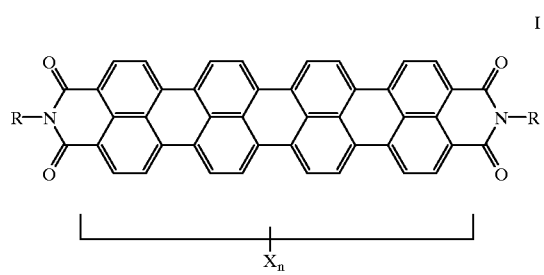

I where

R is hydrogen;
$C_1$–$C_{30}$-alkyl whose carbon chain optionally is interrupted by one or more of —O—, or, —$NR^1$—, and which optionally is monosubstituted or polysubstituted by cyano, $C_1$–$C_6$-alkoxy or a 5-, 6- or 7-membered heterocyclic radical which is attached via a nitrogen atom and which optionally contains additional heteroatoms and optionally is aromatic, where
$R^1$ is hydrogen or $C_1$–$C_6$-alkyl;
$C_5$–$C_8$-cycloalkyl;
aryl or hetaryl, each of which optionally is monosubstituted or polysubstituted by $C_1$–$C_{18}$-alkyl, $C_1$–$C_6$-alkoxy, cyano, —$CONHR^2$, —$NHCOR^2$ and/or aryl-azo, each of which optionally is substituted by $C_1$–$C_{10}$-alkyl, $C_1$–$C_6$-alkoxy or halogen, where
$R^2$ is hydrogen; $C_1$–$C_{18}$-alkyl; aryl, which optionally is substituted by $C_1$–$C_6$-alkyl, $C_1$–$C_6$-alkoxy, halogen or cyano;
X is halogen; $C_1$–$C_{18}$-alkyl; aryloxy, arylthio, hetaryloxy or hetarylthio, each of which optionally is substituted by $C_1$–$C_4$-alkyl or $C_1$–$C_4$-alkoxy;
n is from 2 to 8.

\* \* \* \* \*